United States Patent [19]

Medenica et al.

[11] Patent Number: 5,989,839
[45] Date of Patent: Nov. 23, 1999

[54] USE OF MOLT4 CD69 EXPRESSION TO DETERMINE THE PRESENCE AND ACTIVITY OF INTERFERON INHIBITORS

[75] Inventors: Rajko D. Medenica, New York, N.Y.; David K. Powell, Hilton Head Island, S.C.

[73] Assignee: Ghassan I. Shaker, London, United Kingdom

[21] Appl. No.: 08/914,526

[22] Filed: Aug. 19, 1997

Related U.S. Application Data

[60] Provisional application No. 60/024,173, Aug. 19, 1996.

[51] Int. Cl.$^6$ .............................. G01N 33/53; C12N 5/22; A61K 38/21
[52] U.S. Cl. ...................... 435/7.24; 424/85.4; 424/85.7; 424/154.1; 930/142; 435/372.3
[58] Field of Search ................................ 435/7.24, 372.3; 424/85.4, 85.7, 154.1; 930/142

[56] References Cited

U.S. PATENT DOCUMENTS

| | | | |
|---|---|---|---|
| 5,215,741 | 6/1993 | Young et al. | 424/85.7 |
| 5,270,037 | 12/1993 | Bienzle | 424/85.5 |
| 5,474,771 | 12/1995 | Lederman et al. | 424/133.1 |
| 5,503,987 | 4/1996 | Wagner et al. | 435/7.94 |

OTHER PUBLICATIONS

Gerosa et al. Different sensitivity to interleukin 4 of interleukin 2–and interferon alpha–induced CD69 antigen expression in human resting NK cells and CD3+, CD4−, CD8− lymphocytes. Cellular Immunology, (May 1992) 141 (2) 342–51.

Chorvath et al. Interferon alpha–induced modulation of leukocyte cell surface antigens: immunocytofluorometric study with human leukaemia/lymphoma cell lines. Acta Virologica, (Jan. 1991) 35 (1) 7–18.

Medenica et al. Journal of Clinical Apheresis, 9:216–221 (1994).

Chadha et al. Journal of Biological Regulators and Homeostatic Agents, 5:1–9 (Jan.–Mar. 1991).

Aszalos et al. Biochemical Medicine and Metabolic Biology, 46:267–270 (Oct. 1991).

Havredaki, M. and Barona, F. (1985) "Variations of interferon inactivators and/or inhibitors in human serum and their relationship to interferon therapy," *Japan J. Med. Sci. Biol.* 38: 107–111.

Kawade, Y and Watanabe, Y. (1984) "Neutralization of interferon by antibody: Appraisals of methods of determining and expressing neutralization titer," *J. of Interferon Res.* 4: 571–584.

Rhodes et al., (1984) "Human tumor–induced inhibition of interferon action in vitro: Reversal of inhibition by β–carotene (pro–vitamin A)," *Cancer Immunol. Immunother.* 16: 189–192.

Bjorndahl, J.M., et al. (1988), "The 28 kDa/32 kDa activation antigen EA1; Further characterization and signal requirements for its expression," *J. Immunol.* 141: 4094.

J. Natl. Cancer Inst. (Bethesda) (1972), 49:891–895.

Maino, VC, Suni MA, Ruitenberg, JJ, Rapid Flow cytometric method for measuring lymphocyte subset activation, *Cytometry* (1995), 20(2): 127–133.

Cebrián, M. Yagüe, E., Rincón, M., López–Botet, M., De Landázuri, M.O., Sánchez–Madrid, E., Triggering of cell proliferation through AIM, an acitvation inducer molecule expressed on activated human lymphocytes, *J. Exp. Med.* (1988), 168:1621–1637.

Lanier, L.L., Buck, D.W., Rhodes, L., Ding, A., Evans, E., Barney, C., Phillips, J.H., Interleukin 2 activation of natural killer cells rapidly induces the expression and phosphorylation of the Leu–23 antigen, *J. Exp. Med.* (1988) 1572–1585.

Testi, R., Phillips, J.H., Lanier, L.L., Leu 23 induction as an early marker of functional CD3/T cell antigen receptor triggering: requirement for receptor cross–linking, prolonged elevation of intracellular [Ca++] and stimulation of protein kinase, *J. Immunol.* (1989) 142:1854–1860.

Nakamura, S., Sung, S.S.J., Bjorndahl, J.M., Fu, S.M., Human T cell activation IV. T cell activation and proliferation via the early activation antigen EA–1, *J. Exp. Med.* (1989) 169:677–689.

Santis, A.G., Campanero, M.R., Alonso, J.L., Tugroros, A., Alonso, M.A., Yagüe, E., Pivel, J.P., Sánchez–Madrid, E., TNF—a production induced in T lymphocytes through the AIM/CD69 activation pathway, *Eur. J. Immunol.* (1992), 22:1253–1259.

López–Cabrera, M., Santis, A.G., Fernández–Ruiz, E., Blacher, R., Esch, F., Sánchez–Mateos, P., Sánchez–Madrid, E., Molecular cloning, expression, and chromosomal localization of the human earliest lymphocyte activation antigen AIM/CS69, a new member of the C–type animal lectin superfamily of signal transmitting receptors, *J. Exp. Med.* (1993), 178:537–547.

Full text of the ATCC catalog entry for MOLT 4 cell line.

*Primary Examiner*—Elizabeth Kemmerer
*Assistant Examiner*—David S. Romeo
*Attorney, Agent, or Firm*—DeWitt Ross & Stevens SC

[57] ABSTRACT

Disclosed is a method of determining the presence and activity of interferon inhibitors in a test sample, preferably human blood serum. The method includes the steps of culturing cells which express an interferon-inducible antigen in the presence of an interferon and then adding an aliquot of the cultured cells to a test sample and to a control sample. The expression of the interferon-inducible antigen is then measured in both the test sample and in the control sample and these two values compared to determine the presence and activity of interferon inhibitors in the test sample.

8 Claims, 6 Drawing Sheets

USE OF MOLT4 CD69 EXPRESSION TO DETERMINE THE PRESENCE AND ACTIVITY OF INTERFERON INHIBITORS

Priority is claimed to U.S. provisional patent application Ser. No. 60/024,173, filed Aug. 19, 1996.

FIELD OF THE INVENTION

The invention is directed to a method of determining the presence and activity of interferon inhibitors in a test sample. Where the test sample is human serum, measuring the presence and activity of interferon inhibitors present in the serum provides information on the ability of interferons present in the serum to stimulate immune system activity.

DESCRIPTION OF THE PRIOR ART

Prior research strongly suggests that certain biological factors exist which inhibit either the activity or production, or both, of interferons (IFN). The activity of exogenous IFN is clearly reduced by the presence of these as-yet-uncharacterized IFN inhibitors.

Currently, IFN is used routinely to treat many different disease states, most notably neuro-immunological malignancies and immunodeficiency disorders. It has become particularly clear, however, that the efficacy of IFN treatment in any given patient, as well as any given patient's tolerance to IFN treatment, varies widely. Therefore, it would be useful to determine the potential efficacy and sensitivity of any given patient to IFN treatment. It is believed that the efficacy and patient sensitivity to IFN treatment is greatly effected by the presence of IFN inhibitors in the patients' serum. Therefore, assessing the presence and/or activity of these IFN inhibitors provides useful information on the activity of IFN, either native or exogenous IFN, in a patient's serum.

Prior art techniques for assessing IFN activity per se or the presence of IFN inhibitors fall into three broad categories:

1. Inhibition of Viral Protection: Interferons were so named due to their ability to interfere with viral infection of cells. The most widely used IFN assay involves incubating dilutions of test serum with an amniotic cell line (WISH cells) for a period of time ranging from several hours to 24 hours, followed by addition of a virus which is pathogenic for the WISH cells. Interferon present in the test serum will function to protect infection of the WISH cells by the added virus. The degree to which the WISH cell are protected from the virus, as measured by WISH cell death, is proportional to the amount of IFN in the test serum.

This technique has been adapted to measure IFN inhibitor activity in test serum. Dilutions of test serum are added to an amount of interferon which is known to cause 90–100% protection of the WISH cells when challenged with the virus. The assay is then performed as described above, and the viability of the WISH cells in the presence of the test sera are compared with the viability of WISH cells exposed only to IFN. If the degree of protection from the virus is reduced in the test samples as compared to the controls, the presence of IFN inhibitors in the test samples is confirmed. See Havredaki, M. and Barona, F. (1985) "Variations of interferon inactivators and/or inhibitors in human serum and their relationship to interferon therapy," *Japan J. Med. Sci. Biol.* 38: 107–111; and Kawade, Y and Watanabe, Y. (1984) "Neutralization of interferon by antibody: Appraisals of methods of determining and expressing neutralization titer," *J. of Interferon Res.* 4: 571–584.

2. Inhibition of Monocyte Fc Receptor Expression Measured by Red Cell Rosetting: Interferons are known to increase the expression of Fc receptors on monocytes. The method of Rhodes et al., (1984) "Human tumor-induced inhibition of interferon action in vitro: Reversal of inhibition by β-carotene (pro-vitamin A)," *Cancer Immunol. Immunother.* 16: 189–192, uses antibody-coated erythrocytes to measure the relative amount of monocyte Fc receptor expression. The number of red cells forming rosettes around the monocytes, counted microscopically, is proportional to the number of Fc receptors on the monocyte membrane. The authors use this technique to detect the presence of low molecular weight IFN inhibitors in serum and in the culture supernatant of cell lines. If an inhibitor is present, the number of red cells forming rosettes around the monocytes decreases as compared to controls containing IFN only.

3. Enzyme-Linked Immunosorbent Assay (ELISA) for Interferon Antibodies: Commercial kits are available which detect the presence of antibodies against various IFN's. For example, recombinant IFN-α2a is a form of interferon which is frequently used therapeutically. It has been estimated that approximately 20% of patients so treated develop neutralizing antibodies to the IFN. The commercially available tests employ microplates coated with an IFN in a conventional double-antibody sandwich ELISA format.

SUMMARY OF THE INVENTION

The invention is directed to a method of determining the presence and activity of interferon inhibitors in a test sample. The method comprises the steps of culturing cells which express an interferon-inducible antigen in the presence of an interferon, thereby inducing expression of the interferon-inducible antigen. An aliquot of the cultured cells is then added to a test sample and to a control sample. The preferred test sample is human blood serum from an individual human patient, with the corresponding control sample being an aliquot of pooled human blood serum. The expression of the interferon-inducible antigen in the cultured cells of the test sample and in the cultured cells of the control sample is then measured and compared. Comparing the extent of antigen expressed between the test sample and the control sample quantifies the presence and activity of interferon inhibitors in the test sample.

More specifically, the present invention is also directed to a method of determining the presence and activity of interferon inhibitors in human blood serum comprising the steps of culturing MOLT4 cells, ATCC CRL-1582 (a lymphoblastic leukemia cell line), in the presence of a sufficient amount of interferon α2a to induce CD69 antigen expression in the MOLT4 cells. An aliquot of the cultured MOLT4 cells is then added to a test sample of human blood serum from an individual patient and a control sample of commercially-available pooled human blood serum. An aliquot of fluorophore-labelled monoclonal anti-CD 69 antibody is then added to the test sample and to the control sample. The CD69 antigen expressed on the MOLT4 cells of the test sample and the MOLT4 cells of the control sample is then determined by flow cytometry and the two values compared to determine the presence and activity of interferon inhibitors in the test sample.

A practical utility of the present invention is that it provides a method for determining the potential sensitivity of any given patient to IFN therapy. Those patients who exhibit high IFN inhibitor activity in their serum might then be given larger doses of IFN to overcome the adverse effects of the IFN inhibitor activity and thereby provide a therapeutically-effective dosage of IFN. In contrast, those patients exhibiting little or no IFN inhibitor activity may respond very well to IFN treatments using much smaller doses of IFN, thereby avoiding or minimizing the adverse side effects of the IFN treatment itself. In short, by determining the presence and activity of IFN inhibitors, physicians can adjust therapeutic IFN treatments accordingly.

The method is also useful as a means of indicating the potential presence of autoimmune, viral, or malignant neoplastic disease states in the subject being tested. As presented in the Examples, below, increased activity of IFN inhibitors in the serum generally accompanies such disease states.

The method is also useful for monitoring the efficacy of continued IFN treatments by evaluating the presence of IFN inhibitors in the patient over the course of therapy. As the activity of IFN inhibitors decreases, the dosage of IFN administered can be decreased accordingly.

The main advantage of the present method is that it provides an efficient, rapid, and easily performed in vitro assay to measure the presence and activity of factors which adversely impact the biological activity of endogenous or exogenous IFN.

These and other advantages of the present invention will become apparent upon a complete reading of the "Detailed Description" and attached claims.

DETAILED DESCRIPTION OF THE INVENTION

Figure 1:
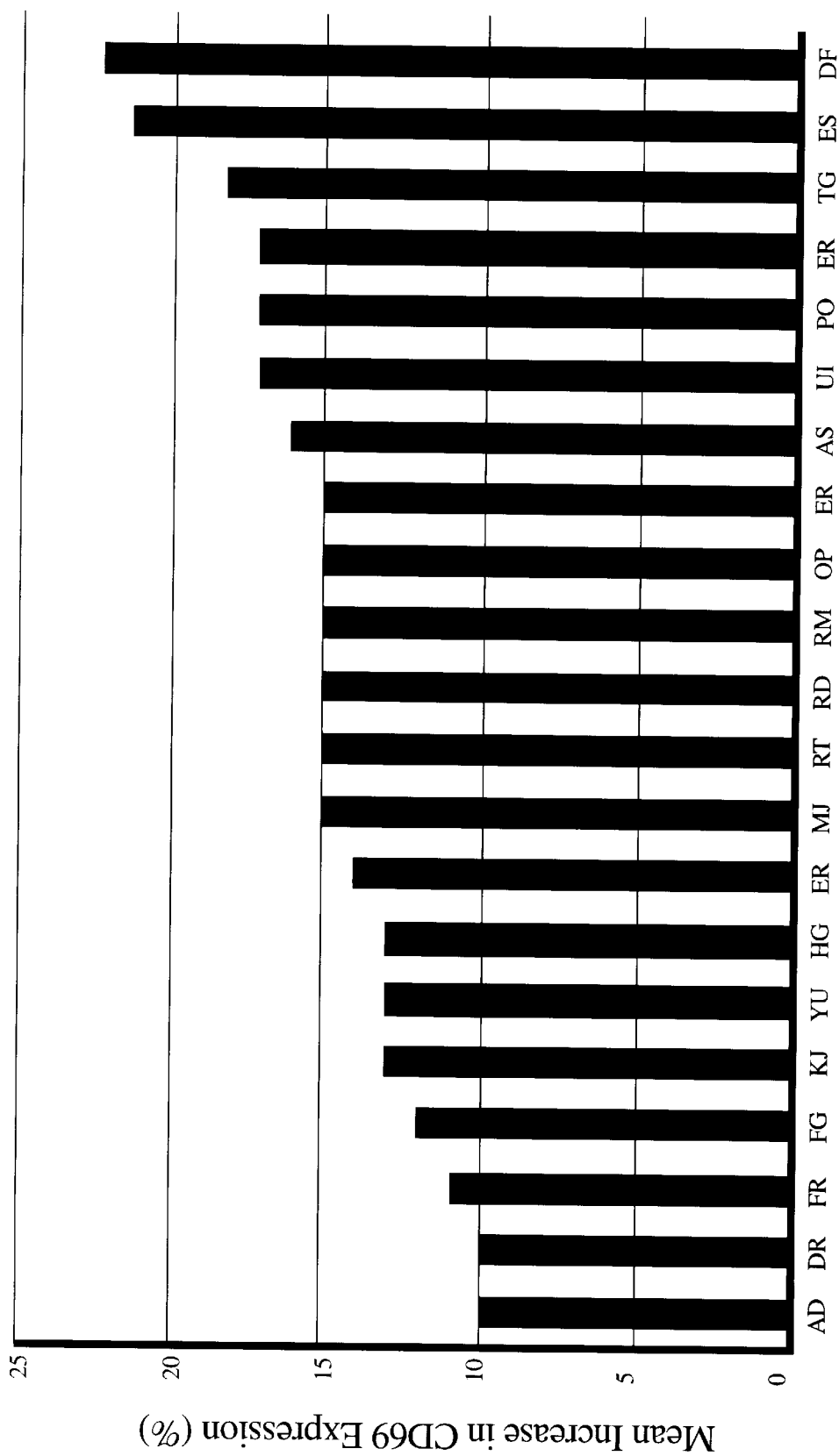
FIG. 1 is a graph depicting the mean increase in CD69 expression in MOLT4 cells cultured in the presence of IFN α2a and serum from 21 healthy donors. See Example 1.

Definitions:

The following definitions are included to provide a clear and consistent understanding of the meaning and scope of certain terms used throughout this specification.

"Anti-CD69 Monoclonal Antibody", "Anti-CD69 mAb": a monoclonal antibody specific for the CD69 antigen. Phycoerythrin-labelled anti-CD69 mAb is available commercially from Becton Dickinson, Mountain View, California (Cat. # 347827). The L78 clone employed by Becton Dickinson to produce this antibody is derived from the hybridization of mouse Sp2/0-Ag14 myeloma cells with lymph node cells from BALB/C mice immunized with a CD8 + alloantigen-directed cytotoxic T-lymphocyte cell line. The immunoglobulin chain composition of the antibody is mouse IgG1 heavy chains and kappa light chains.

"CD69 antigen" or "CD69 molecule": a surface-bound antigen which is expressed by virtually all T cells upon activation. The CD69 antigen is a heterodimer containing a 32 kDa subunit and a 28 kDa subunit which are linked via a disulfide bridge. Under normal culture conditions, the CD69 antigen is readily expressed by MOLT4 cells upon activation.

"Interferon(s)", "IFN(s)": a family of over 50 closely related glycoproteins which display antiviral, immunoregulatory, and antiproliferative activity. As used herein, the term encompasses all interferon types and subtypes, from any source, including human, non-human, and recombinant interferons. The immunoregulatory functions of interferons, such as enhancing natural killer lymphocyte activity, increasing expression of histocompatibility antigens, activating monocytes and macrophages, and regulating other B cell functions, have proven to be of clinical importance. For example, IFN has been used to protect bone marrow from the toxicity of chemotherapy. As a further example of therapeutic applications of IFN, treatment with IFN alone or in combination with other drugs increases the occurrence of clinical remission in diseases such as hairy-cell leukemia, chronic myelogenic leukemia, non-Hodgkin's lymphoma, and multiple myeloma.

"Interferon (IFN) Inhibitors" or "Interferon Inhibitor Factors": agent or agents found in animal sera which inhibit the production and/or activity of IFN's. In the case of exogenous IFN's, IFN inhibitors inhibit the biological activity of the added IFN. Research suggests that in patients suffering from certain disease states, IFN inhibitors are either produced simultaneously with the production of endogenous IFN, thereby limiting the beneficial activity of the IFN, or the IFN inhibitors function to reduce the production of endogenous IFN. In either event, the overall biological activity of IFN inhibitors is to inhibit the activity of IFN.

"MOLT4": a T lymphoblastic leukemia cell line available from the American Type Culture Collection, 12301 Parklawn Drive, Rockville, Md., 20852, Accession No. ATCC CRL-1582. Like the vast majority of T cells, this cell line can be rapidly induced to express the surface antigen CD69. See, for instance, Bjorndahl, J. M., et al. (1988), "The 28 kDa/32 kDa activation antigen EA1; Further characterization and signal requirements for its expression," *J. Immunol.* 141: 4094.

Methodology:

The invention is an in vitro method which utilizes the inhibition of the expression of an IFN-inducible antigen to measure the presence and activity of IFN inhibitors. When exposed to IFN, immune-competent cells will be activated and express certain IFN-inducible antigens on their cell surfaces. However, when IFN inhibitors are present, which is the case when the patient is suffering from various disease states, expression of the IFN-inducible antigen is inhibited due to the interaction between IFN and the IFN inhibitors. In effect, the cells are shielded from the biological effects of IFN. Therefore, determining the extent of the inhibition of the expression of the IFN-inducible antigen provides quantitative data on the presence and activity of IFN inhibitors present in the sample. By comparing the extent of inhibition in a test sample and comparing the amount of inhibition to a control sample lacking IFN inhibitors, the IFN inhibitory activity in the test sample can be determined.

The first step of the method is to culture in vitro cells which express an interferon-inducible antigen in the presence of an interferon, thereby inducing expression of the interferon-inducible antigen. The preferred cell line for culture is the lymphoblastic leukemia cell line MOLT4. This cell line will readily express the CD69 antigen upon exposure to an activating concentration of IFN.

While the following description will be limited to the use of the preferred MOLT4 cell line, this abbreviated discussion is for brevity and clarity only. Several cell lines expressing various IFN-inducible antigens can be utilized in the claimed method. The MOLT4 cell line is preferred for its ready growth in culture and its predictable expression of the CD69 antigen. However, other cell lines and expressing other IFN-inducible antigens can be used with equal success.

The preferred IFN for use in the present invention is IFN $\alpha$2a. However, other sub-types of IFN's can also be utilized with success.

An aliquot of the cultured cells is then added to a test sample and to a control sample. The cells/sample mixture is then cultured in vitro for anywhere from about 24 to about 72 hours under standard culture conditions (37° C., 5% $CO_2$, 100% humidity).

The preferred test sample is human blood serum from an individual human patient. The corresponding preferred control sample is an aliquot of pooled human blood serum from healthy individuals.

The expression of the interferon-inducible antigen in the cultured cells of the test sample and in the cultured cells of the control sample is then measured and compared. Comparing the extent of antigen expressed between the test sample and the control sample quantifies the presence and activity of interferon inhibitors in the test sample.

Measuring the extent of antigen expression in the test and control samples is most easily and accurately accomplished via flow cytometry. This procedure is greatly preferred for its flexibility, efficiency, and speed. When using cells which express the preferred CD69 antigen, cells expressing the CD69 antigen can be readily determined by exposing the cells to a saturating amount of fluorphore-tagged anti-CD69 mAb. The mAb is specific for CD69 and will bind to those cells which express the antigen. The cells expressing CD69 are then identified by the signature fluorescent signal emitted by the fluorophore when excited by laser light of the proper wavelength. The preferred fluorophore is phycoerythrin, which emits radiation at 580 nm when excited by a 488 nm light source.

Any other quantitative device or protocol which yields equivalent data regarding the expression of a particular antigen can also be used. The method of determining the amount of expressed antigen is not critical, so long as the method yields accurate and precise data.

In the most preferred embodiment of the method, the presence and activity of interferon inhibitors in human blood serum are quantified. In the first step, a stock culture of MOLT4 cells, ATCC CRL-1582, is established in the presence of a sufficient amount of IFN $\alpha$2a to induce CD69 antigen expression in the MOLT4 cells. An aliquot of the cultured MOLT4 cells is then added to a test sample of human blood serum from an individual patient and a control sample of commercially-available pooled human blood serum. An aliquot of fluorophore-labelled monoclonal anti-CD69 antibody is then added to the test sample and to the control sample. The CD69 antigen expressed on the MOLT4 cells of the test sample and the MOLT4 cells of the control sample is then determined by flow cytometry and the two values compared to determine the presence and activity of interferon inhibitors in the test sample.

EXAMPLES

The following Examples are included solely to aid in a more complete understanding of the present invention. The Examples do not limit the scope of the invention described and claimed herein in any fashion.

The following exemplary reagents and equipment and a commercial supplier for each were used in the Examples. Equivalent reagents and equipment are available from several other national and international commercial suppliers.

Flow cytometer: "FACScan" model, from Becton Dickinson, Mountain View, Calif., USA.

Anti-CD69 monoclonal antibody: Phycoerythrin-conjugated anti-CD69 monoclonal antibody from Becton Dickinson, Mountain View, Calif., catalog no. 347827. Anti-IFN antibody: Sheep anti-human polyclonal antibody against human interferon alpha from Sigma Corporation, St. Louis, Mo., USA.

Recombinant IFN $\alpha$2a (3,000,000 units/mL): available from Roche Laboratories, a division of Hoffman-LaRoche Inc., Nutley, N.J., USA under the registered trademark "ROFERON-A." MOLT4 T cell leukemia cells: ATCC CRL-1582; maintained in suspension culture and used at a concentration of $2\times10^6$ cells/mL. The passage number of the MOLT-4 cells should be kept below 300 after receipt of this cell line from the ATCC. It is preferred that the viability of the MOLT-4 cells to be used in the method be greater than 90%. If the viability of the cells is less than 90%, the sensitivity of the test could be adversely affected.

Lyophilized human pooled serum was purchased from Sigma Corporation.

Reagent Preparation—

| RPMI 1640 Medium: 10% RPMI 1640 (1X) G,G fortified, all components are available from Sigma Corporation: | |
|---|---|
| AMOUNT | COMPONENT |
| 500.0 ml | RPMI Medium 1640 (1X), liquid with L-Glutamine |
| 50.0 ml | Fetal Bovine Serum |
| 5.0 ml | Penicillin-Streptomycin, liquid |
| 10,000 units/ml | Penicillin |
| 10,000 µg/ml | Streptomycin |
| 5.0 ml | L-Glutamine-200 mL (100x), liquid |
| 5.0 ml | Insulin-Transferrin-Sodium Selenite Media Supplement |

All of the above components are combined and thoroughly mixed under a sterile laminar flow hood. Phenol red is used to perform a visual check of medium color for appropriate pH. The prepared medium is stable for 3 months when refrigerated at 2–8° C.
Patient Culture Medium:

| AMOUNT | COMPONENT |
|---|---|
| 500 mL | RPMI 1640 (1X) with L-Glutamine |
| 500 mL | Iscove's modified Dulbecco's medium (IMDM) |
| 100 mL | fetal bovine serum |
| 10 mL | L-Glutamine |
| 10 mL | Perncillin-Streptomycin |
| 5 mL | Minimal essential Vitamin solution (13-607C BioWhittaker) |
| 5 mL | Insulin-Transferrin-Sodium selenite supplement |

250.0 mL of RPMI (1x) and 250.0 mL of IMDM in sterile graduated cylinders are combined under a sterile laminar flow hood into a 500.0 mL sterile filter with a 0.22 mm cellulose acetate membrane with a 60 mm prefilter. Fetal bovine serum (FBS) is added with sterile disposable pipettes. All other ingredients listed are added immediately prior to use. Phenol red is used to perform a visual check of medium color for appropriate pH. The prepared medium is stable for 3 months when refrigerated at 2–8° C.

IFN α2a:

If supplied in lyophilized form, the IFN α2a should be reconstituted following the manufacturer's instructions. Stock solution concentrations may differ by supplier. 100 μL of IFN α2a ($3\times10^6$ U/mL) are added to a sterile 14 mL tube and 9.9 mL of 10% RPMI added. The tube is thoroughly mixed. The resulting solution contains 30,000 U/mL IFN. 100 μL of the first dilution is added to another 14 mL tube, and a further 9.9 mL of 10% RPMI is added. The tube is again mixed. The resulting solution contains 300 U/mL. Three (3) mL of the 300 U/mL IFN solution is added to a 50 mL graduated conical tube and 42 mL of Patient Culture Medium (defined above) is added. The tube is mixed for 5–10 seconds. The resulting solution contains a working concentration of IFN α2a. Aliquots of the working solution (1.5 mL) are dispensed into 6 mL sterile tubes with caps and can be stored at −40° C. for up to 3 months.

Sheep Anti-Human Polyclonal Antibody:

Sheep anti-human polyclonal antibody is stored in 3 mL aliquots of 1,000 neutralizing units/mL at −40° C. until ready for use. It is then thawed at 37° C. and mixed by inversion until all protein has been resuspended. A 2 mL aliquot of the thawed antibody is added to a 50 mL sterile tube, and 38 mL Patient Culture Medium is added. The tube is mixed for 5–10 seconds. The resulting solution now contains a working concentration of 50 neutralizing units/mL. Aliquots of the working solution (1.5 mL) are dispensed into 6 mL sterile tubes with caps and can be stored at −40° C. for up to 6 months.

Phycoerythrin-labelled CD69 Monoclonal Antibody:

Immediately before use, the antibody is diluted 1 to 3 in phosphate-buffered saline (PBS) in a 6 mL capped tube and gently mixed.

Flow Cytometry Fixative:

Paraformaldehyde, 2.5 g, is added to 500 mL PBS and placed on a magnetic stirrer until dissolved. It may be stored at room temperature for up to 3 months.

Lyophilized Human Pooled Serum:

Lyophilized human pooled serum is prepared according to the manufacturer's instructions by adding an appropriate amount of sterile deionized or distilled water to the lyophilized powder and allowing it to stand, with occasional mixing, until dissolved. 100 μL aliquots of the reconstituted serum are dispensed into 6 mL sterile, capped tubes which can be stored at −40° C. for up to 12 months.

Whole Blood Specimen Collection:

Whole blood is collected into a serum separation tube and allowed to clot. The specimen is then centrifuged at 3,000 rpm for 5 minutes followed by serum removal. If not tested immediately, the serum should be frozen at −20° C. or lower until it is tested.

Preparation of Serum Test Specimens:

All frozen reagents are thawed and thoroughly mixed before use, according to procedures described above. The Examples provided herein were performed using human blood serum as a test sample. The same protocol will function with equal success on other biological samples suspected of containing IFN inhibitors (i.e., other bodily fluids, cells extracts, culture supernatants and the like.

Aliquots (20 μL) of pooled human serum is pipetted into a first series of centrifuge tubes to act as the control. Aliquots (20 μL) of serum from an individual patient is pipetted into a parallel series of centrifuge tubes. At least one tube of the control serum and the test serum are set aside for negative controls. Patient Culture Medium (900 μL) is added to the negative control tubes.

A first series of samples was then constructed in which the control serum and the test serum was mixed with IFN: IFN α2a (100 μL of 20 units/mL) is added to at least one tube each of the control serum and the test serum. These tubes are labelled "S+IFN" (control or test). Patient Culture Medium (800 μL) is added to each of these tubes.

A second series of samples was then constructed in which the control serum and the test serum was mixed with anti-IFN antibodies in the same fashion as described immediately above for IFN. These tubes are labelled "S+Anti-IFN" (control or test).

MOLT4 T cell leukemia cells, 100 μL at a concentration of $2\times10^6$ cells/mL was then added to each tube and the tubes incubated at 37° C. in 5% $CO_2$ for 48 hours. A summary of the samples assembled appear as follows:

| | SERUM ONLY TUBE μL | SERUM + IFN TUBE(μL) | SERUM + Anti-IFN TUBE(μL) |
|---|---|---|---|
| MEDIUM | 900 | 800 | 800 |
| 20 U/mL IFN | 0 | 100 | 100 |
| SERUM | 20 | 20 | 20 |
| MOLT4 CELLS | 100 | 100 | 100 |

Following incubation, the samples are centrifuged and the supernatant is removed. Diluted CD69 monoclonal antibody (10 μL) is added to each tube and incubated in the dark for 15 minutes. The cells are washed once in 1 mL PBS, pH 7.2, and then resuspended in 0.5 mL 0.5% paraformaldehyde for flow cytometric analysis.

Flow Cytometric Analysis:

Any commercially available flow cytometer capable of detecting phycoerythrin fluorescence (FL2) emitting at 580 nm when excited by a 488 nm light source is acceptable for use. In common flow cytometers, a cell suspension is hydrodynamically forced into a stream wherein cells pass by a focal point one by one. A laser is focused upon this focal point, and as a cell passes in front of the laser, the laser light is scattered in a variety of directions. The scattered light is collected and amplified by collection optics/detectors and converted into electrical impulses. The electrical impulses can then be decoded by computer and analyzed to convey information about the cells. The flow cytometer can count the cells in the suspension and collect information on different characteristics of the cells within the suspension by detecting dyes and other markers with which the cells have been treated. For example, cell subpopulations may be excluded from certain flow cytometric analyses by marking the subpopulations and having the flow cytometer gate (subtract) them from the analysis. Despite the foregoing description of the construction and operation of a flow cytometer, it is understood that the invention may use any type of cytometer that duplicates the essential functions of the flow cytometer described. The flow cytometer utilized in the present samples was the "FACSCAN" Immunocytometry Systems flow cytometer (Becton Dickinson, Mountain View, Calif., USA) running Becton Dickinson "CELLQUEST" software on a "MACINTOSH QUADRA 650" computer. Other suitable flow cytometers include the "COULTER XL" brand (Coulter Electronics, Hialeah, Fla., USA) or the "ORTHO CYTRON" brand (Ortho Diagnostic Systems, Raritan, N.J., USA).

"FACSCAN" Cytometer Settings:

Linear forward scatter and side scatter voltages were set so that the MOLT4 dot plot appeared in the center of the FSC and SSC plot. The log FL-2 detector voltage was set so that the median of the FL-2 log histogram using the pooled serum tube appeared at approximately 500. Compensation is not set because these were single color analyses. Cell samples were collected (25,000 cells each) and the medians of the log FL-2 histograms were used as a basis for calculating the results.

Result Calculation:

The coefficient of variation for 10 specimens tested in duplicate was 5.6%. The mean result of the duplicate tests is used in the following calculation:

% change in median CD69 expression=

$$\% \text{ change in median CD69 expression} = \frac{(\text{Test Serum} + \text{IFN} - \text{Test Serum without IFN})}{\text{Test Serum without IFN}} \times 100$$

Result Acceptance Criteria:

Based on repeated trials using serum from both healthy individuals and commercially purchased pooled human serum, the controls samples should normally exhibit an increase in median CD69 expression of at least about 9.5% in the presence of IFN. In the case of pooled serum, if CD69 expression does not increase at least about 9.5% in the controls, it is preferred that the tests be repeated using a different batch of pooled human serum. The increase in CD69 expression is serum batch sensitive and must be re-calculated for each new batch of control serum.

Example 1

Establishing a Reference Range

Twenty-one healthy subjects were used for establishing a normal range of increased CD69 expression for reference purposes. The above-described protocol for flow cytometric analysis was applied to serum taken from each of these individuals. The purpose here was to establish a reference range of IFN activity against which test samples could be compared.

For each normal specimen, the median CD69 fluorescence obtained after incubation of patient serum in the presence of 20 U/mL IFN α2a was compared to the median CD69 expression obtained from the tubes containing patient serum only. The mean increase in CD69 expression for these 21 normal subjects is presented in FIG. 1. The overall mean increase in CD69 expression was 14.5%, with the range extending from a 9.5% increase to a 21.8% increase.

As noted above, based upon these results, if the presence of IFN fails to increase CD69 expression in the MOLT4 cells of any given test sample by at least about 9.5%, then that sample is deemed to possess IFN inhibitors.

Example 2

Confirmation that IFN α2a is Responsible for Increase in CD69 Expression

Figure 2:
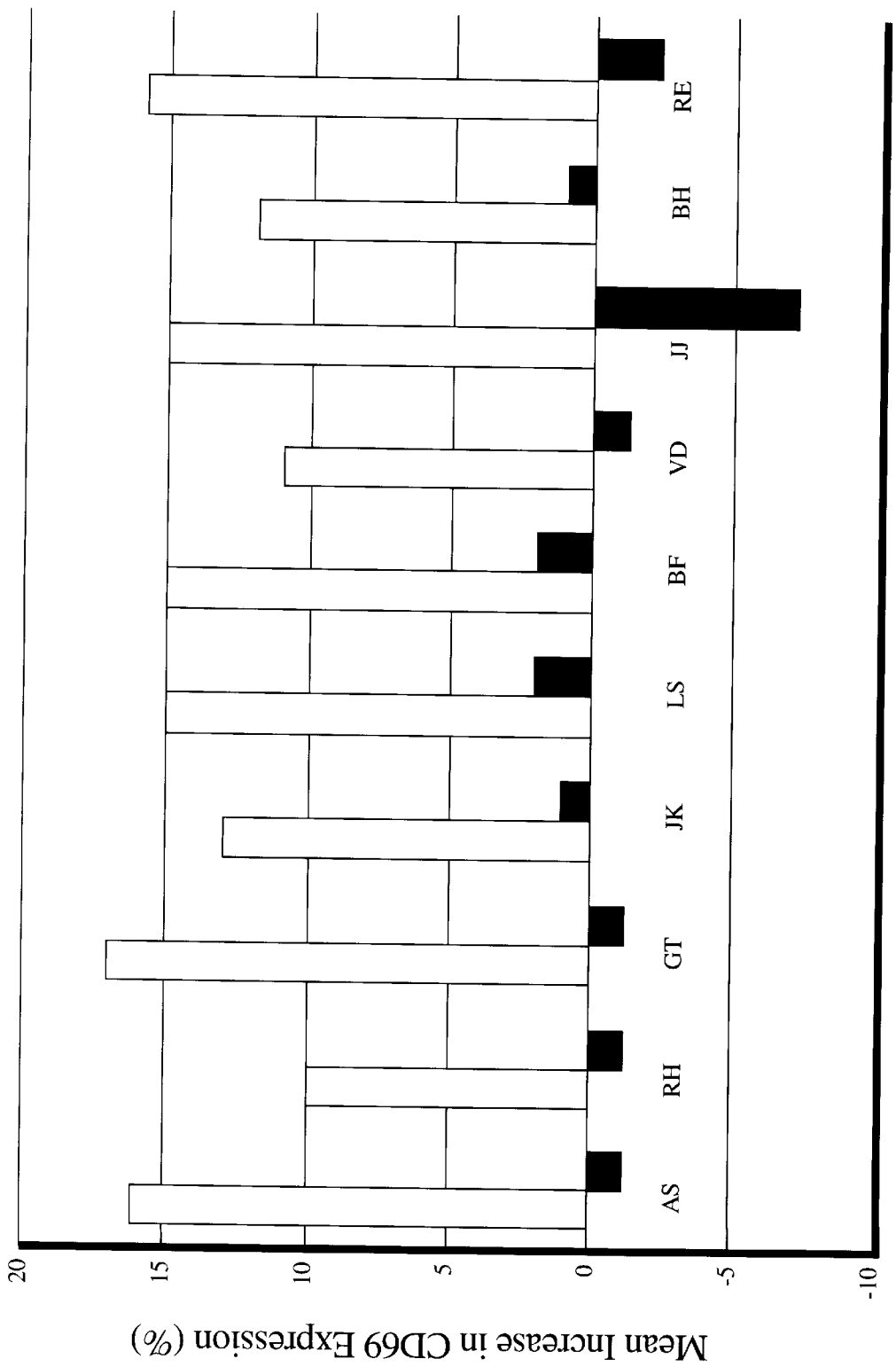
FIG. 2 is a graph depicting the inhibition of IFN's ability to induce expression of the CD69 antigen in MOLT4 cells by the addition of an anti-IFN antibody to the culture. See Example 2.

Using the standard protocol described above, three samples were constructed in duplicate for each of 10 normal specimens:

1. Serum alone
2. Serum+20 μ/mL IFN α2a
3. Serum+20 μ/mL IFN α2a+50 U/mL anti-IFN antibody The aim of this experiment was to confirm that interferon is responsible for the increase in CD69 expression in the MOLT4 cells. The results are shown in Table 1 below, and presented graphically FIG. 2.

The second column of Table 1 indicates the percentage increase in median fluorescent activity attributed to the addition of 20 μ/mL IFN α2a to serum as compared to the fluorescent activity of the serum alone. The third column of Table 1 shows the result of adding an anti-IFN to the tubes containing serum and interferon. In each case the increase in activity (i.e., CD69 expression) attributed to the addition of IFN is considerably diminished.

TABLE 1

| Specimen # | % Change w/IFN | % Change w/IFN & Antibody Against IFN |
|---|---|---|
| 1 | 16.2 | 0.6 |
| 2 | 9.9 | −0.4 |
| 3 | 16.5 | −0.8 |
| 4 | 12.7 | 1.2 |
| 5 | 14.5 | 2.2 |
| 6 | 15.2 | 1.5 |
| 7 | 11.4 | 0.1 |
| 8 | 14.8 | 0.7 |
| 9 | 12.4 | 1.3 |
| 10 | 15.8 | −1.8 |
|  | MEAN | MEAN |
|  | 13.94 | 0.46 |

Example 3

CD69 Expression in Autoimmune Disease Patients in Remission

Figure 3:
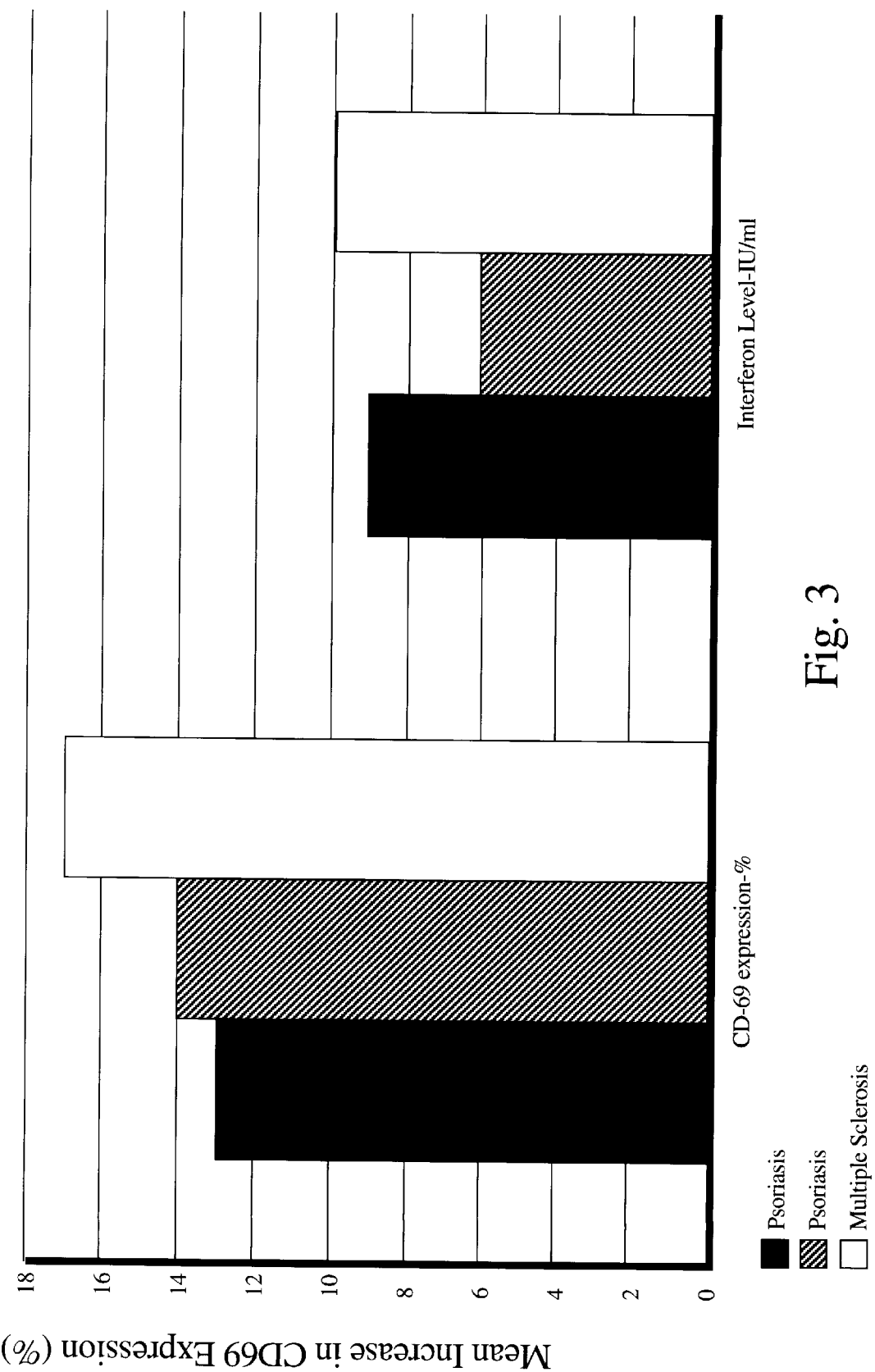
FIG. 3 is a graph depicting the mean increase in CD-69 expression in MOLT4 cells cultured in the presence of patient serum as compared to CD69 expression in control MOLT4 cell cultures (left-hand histogram) and IFN activity (right-hand histogram) in serum from three patients having autoimmune diseases in remission: two having remitted psoriasis and one having remitted multiple sclerosis.

In this Example, serum from three patients having autoimmune diseases in remission, two having remitted psoriasis and one having remitted multiple sclerosis, was subjected to the subject method as described above. The mean increase in CD-69 expression in MOLT4 cells cultured in the presence of patient serum as compared to CD69 expression in the control MOLT4 cell cultures is presented in FIG. 3. The left-hand histogram of FIG. 3 represents the mean increase in CD69 expression, the right-hand histogram represents the level of endogenous IFN found in the individual serum samples (U/mL). suffering from autoimmune diseases and being in remission. Each of these patients, whose autoimmune conditions were in remission, displayed a mean increase in CD-69 expression well in excess of the 9.5% threshold level noted above. These results indicate that little or no IFN inhibitors are present in the serum of these patients. In effect, the serum of these patients is indistinguishable from healthy individuals.

Example 4

CD69 Expression in Cancer Patients in Remission

Figure 4:
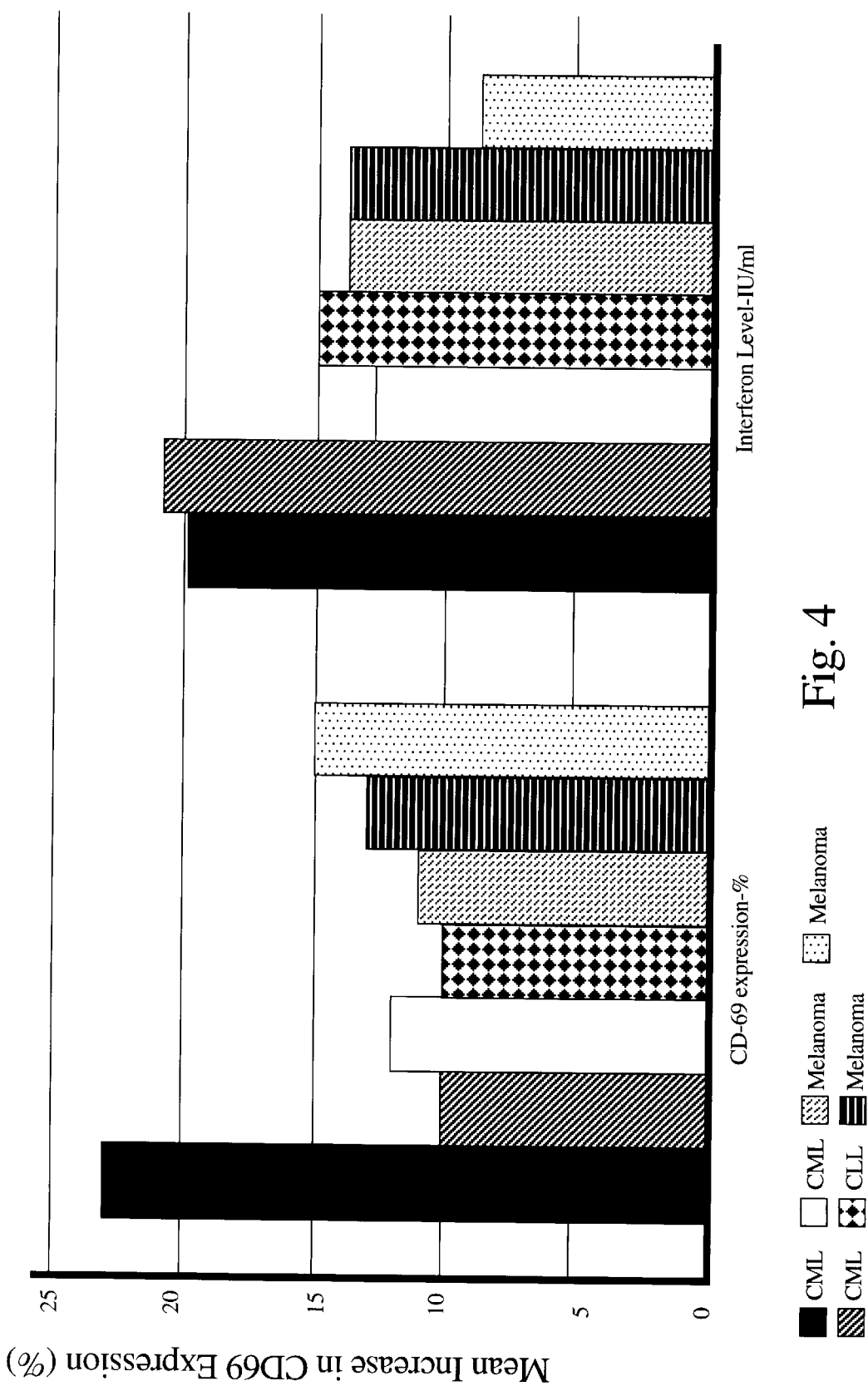
FIG. 4 is a graph depicting CD69 expression in 7 patients having malignant cancers in remission. The left-hand histogram represents the mean increase in CD69 expression, the right-hand histogram represents the level of endogenous IFN found in the individual serum samples (U/mL). The patient population consisted of 3 patients suffering from chronic myelogenic leukemia (CML), 1 patient suffering from chronic lymphocytic leukemia (CML), and 3 patients suffering from malignant melanoma. All 7 patients were in remission.

This Example is identical to Example 3 with the exception that 7 patients having malignant cancers in remission were used as the test subjects. The left-hand histogram of FIG. 4 represents the mean increase in CD69 expression, the right-hand histogram represents the level of endogenous IFN found in the individual serum samples (U/mL). The patient population consisted of 3 patients suffering from chronic myelogenic leukemia (CML), 1 patient suffering from chronic lymphocytic leukemia (CML), and 3 patients suffering from malignant melanoma. All 7 patients were in remission.

As can be seen from FIG. 4, all of these patients, whose malignant conditions were in remission, displayed mean increases in CD69 expression which were in excess of the 9.5% threshold noted above. These results indicate that little or no IFN inhibitors are present in the serum of these patients. In effect, the serum of these patients is indistinguishable from healthy individuals.

Example 5

Comparison of CD69 Expression in Patients Suffering Active Disease States and Patients in Remission In this Example, the standard protocol was performed on the serum of a 14 patients suffering from active disease states and 10 patients whose disease states were in remission. The disease states represented include psoriasis, multiple sclerosis, acquired immune-deficiency syndrome (AIDS), hepatitis C, myeloma, chronic myelogenic leukemia (CML), chronic lymphocytic leukemia (CLL), melanoma, stomach cancer, breast cancer, and prostate cancer. The mean increase in MOLT4 CD69 expression was determined for each patient (left-hand histogram) as well as the level of IFN (right-hand histogram).

Figure 5:
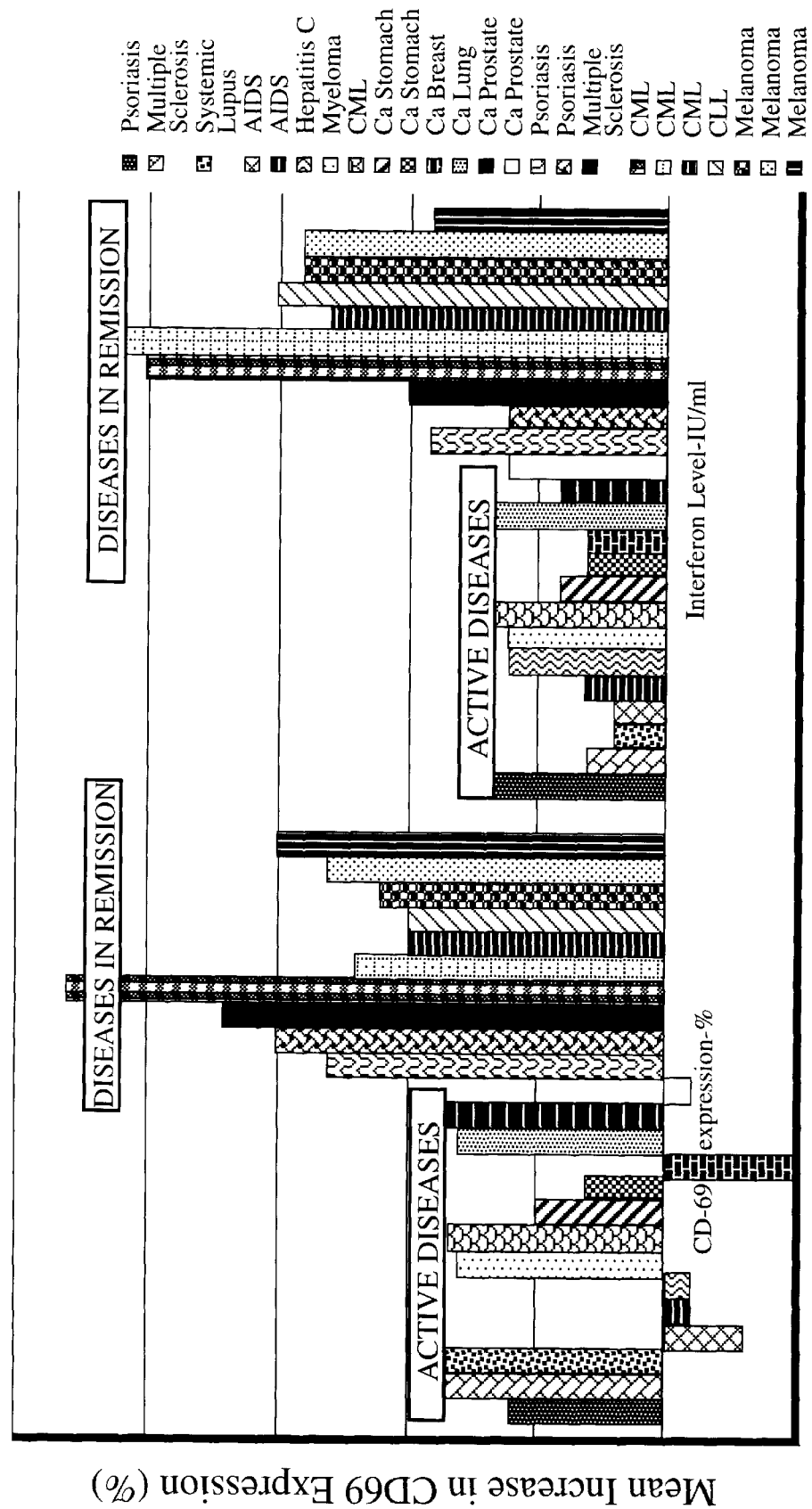
FIG. 5 is a graph depicting a comparison of CD69 expression in patients suffering various active disease states versus patients in remission. The method described herein was performed on the serum of a 14 patients suffering from active disease states and 10 patients whose disease states were in remission. The disease states represented are psoriasis, multiple sclerosis, acquired immune-deficiency syndrome (AIDS), hepatitis C, myeloma, chronic myelogenic leukemia (CML), chronic lymphocytic leukemia (CLL), melanoma, stomach cancer, breast cancer, and prostate cancer. The mean increase in MOLT4 CD69 expression is presented for each patient (left-hand histogram) as well as the level of IFN (right-hand histogram). See Example 5.

As can be readily ascertained from FIG. 5, the first 14 patients, those with active disease states, display increases in CD-69 expression which are much less than the 9.5% threshold level. These patients are actively experiencing a pathological disease state. In several instances, decreases in CD69 expression were shown. This suggests that the IFN inhibitor factors in large amounts (or large activities) appears not only to inhibit IFN activity, but may also reduce CD-69 expression in and of itself.

In contrast, all of the patients presenting with a disease in remission (i.e. the last 10 patients), displayed an increase in CD-69 expression normal in excess of the 9.5% threshold increase. There is also displayed a clear difference between the circulating IFN level in patients with active disease states as compared to patients in remission; patients in remission present a higher IFN circulating level.

This Example clearly demonstrates the utility of the subject method to predict the presence of active disease states.

Example 6

Figure 6:
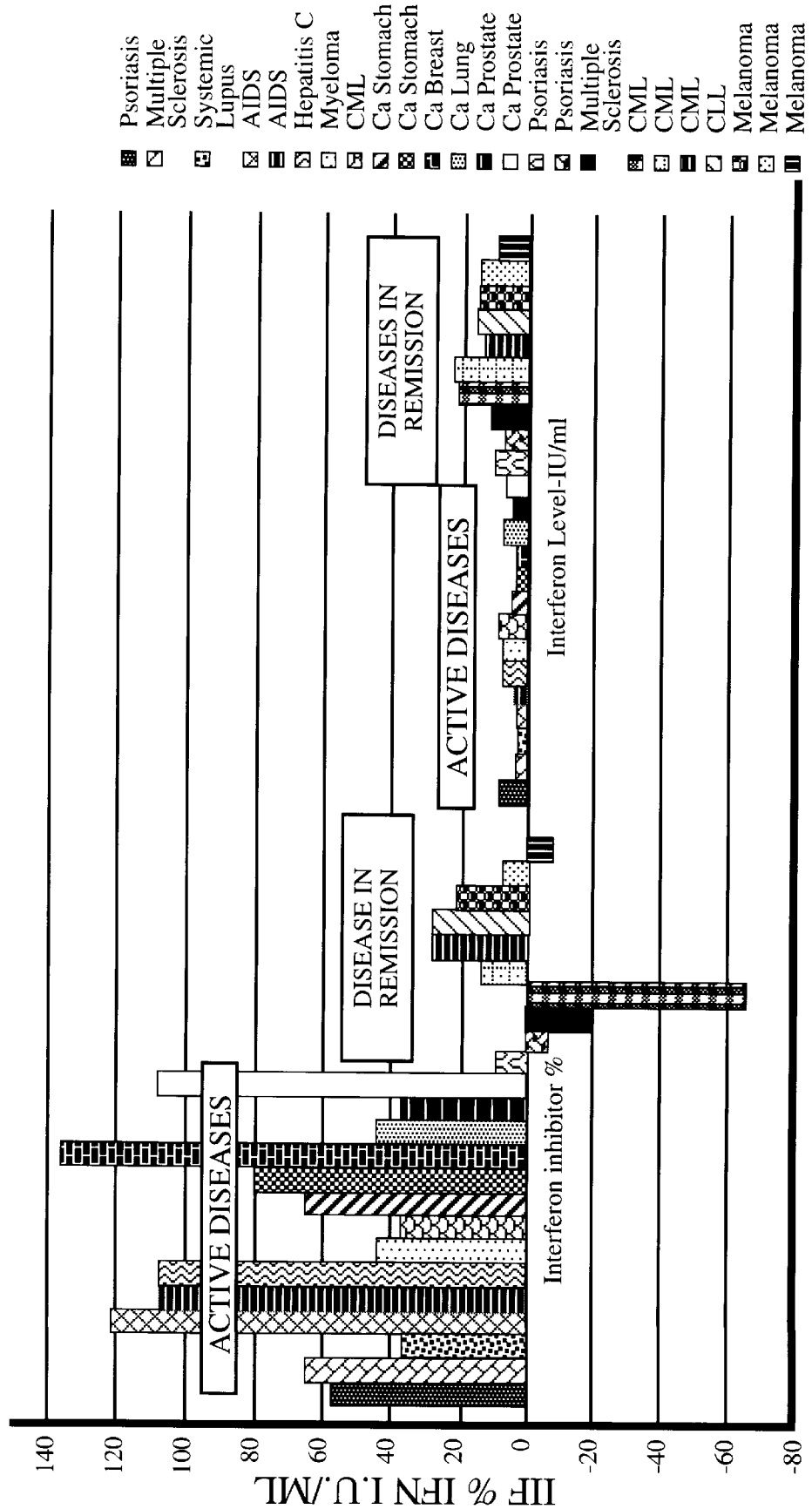
FIG. 6 is a graph depicting the calculated level of IFN inhibition as a percentage of the activity of IFN in the controls in the same patient population of Example 5. As in FIG. 5, this sample included 14 patients suffering active disease states versus 10 patients in remission.

Comparison of IFN Inhibition in Patients Suffering Active Disease States and Patients in Remission Here, the calculated level of IFN inhibition as a percentage of the activity of IFN in the controls is presented for the patient population of Example 5. Again, this sample included 14 patients suffering active disease states versus 10 patients in remission. See FIG. 6. The left-hand histogram presents the percentage of IFN inhibitor as a percentage of IFN activity (U/mL) for both patient groups, the right-hand histogram presents the IFN level for both patient groups.

In those patients whose disease states were in remission, the IFN inhibitor factor activity is well in excess of 25% of the controls. These 14 patients were actively undergoing a pathological disease state.

In contrast, in the 10 patients in remission presented in this Example, the IFN inhibitor activity did not exceed 25%. In fact, an IFN inhibitor activity greater than 25% was never found in any of the other healthy individuals or individuals in remission tested with the subject method.

This Example is an excellent comparison demonstrating that IFN inhibitor activity is greatly elevated only in patients presenting active disease states. With respect to IFN, here again there is a clear difference between the two patient populations in that the IFN level is higher in patients in remission.

The invention disclosed and claimed herein is not limited to the reagents and cell lines specifically described, but includes all variations and equivalent embodiments thereof which are encompassed by the following claims.

What is claimed is:

1. A method of detecting an inhibitor of the biological activity of interferon in a test sample, the method comprising:
   (a) culturing MOLT4 cells ATCC CRL-1582, in the presence of an exogenous interferon, whereby CD69 antigen expression is induced by exposure to the exogenous interferon; then
   (b) adding an aliquot of the cultured MOLT4 cells to a test sample; and
   (c) adding an aliquot of the cultured MOLT4 cells to a control sample; and then
   (d) measuring expression of the CD69 antigen in the cultured cells of the test sample and in the cultured cells of the control sample and comparing the expression of the CD69 antigen in the test sample to expression of the CD69 antigen in the control sample, wherein a decrease in the expression of the CD69 antigen in the test sample as compared to expression of the CD69 antigen in the control sample indicates the presence and activity of an inhibitor of the biological activity of the exogenous interferon.

2. The method of claim 1, wherein in step (d), expression of the CD69 antigen is measured by adding an aliquot of labelled anti-CD69 antibody to the test sample and to the control sample and determining the amount of anti-CD69 antibody bound to the cultured cells of the test sample and the control sample.

3. The method of claim 2, wherein an aliquot of monoclonal anti-CD69 antibody is added to the test sample and to the control sample.

4. The method of claim 2, wherein an aliquot of fluorescently-labelled anti-CD69 antibody is added to the test sample and to the control sample.

5. The method of claim 2, wherein in step (d), the amount of anti-CD69 antibody bound to the cultured cells of the test sample and the control sample is determined by flow cytometry.

6. The method of claim 2, wherein in step (b), the cultured cells are added to a test sample of human blood serum.

7. The method of claim 1, wherein in step (a), the MOLT4 cells are cultured in the presence of interferon α2a.

8. A method of detecting an inhibitor of the biological activity of interferon in human blood serum comprising:

(a) culturing MOLT4 cells, ATCC CRL-1582, in the presence of a sufficient amount of exogenous interferon α2a to induce CD69 antigen expression in the MOLT4 cells; then (b) adding an aliquot of the cultured MOLT4 cells to a test sample of human blood serum; and (c) adding an aliquot of the cultured MOLT4 cells to a control sample of pooled human blood serum; and then (d) adding an aliquot of fluorophore-labelled monoclonal anti-CD69 antibody to the test sample and to the control sample; and then (e) measuring CD69 antigen expressed on the MOLT4 cells of the test sample and the MOLT4 cells of the control sample by flow cytometry and comparing the same, wherein a decrease in the expression of the antigen in the test sample as compared to expression of the antigen in the control sample indicates the presence and activity of an inhibitor of the biological activity of the exogenous interferon.

* * * * *